(12) United States Patent
Franks

(10) Patent No.: US 11,980,736 B2
(45) Date of Patent: May 14, 2024

(54) INFUSION PUMP FLOW RATE CONTROL

(71) Applicant: CareFusion 303, Inc., San Diego, CA (US)

(72) Inventor: Brett Franks, San Diego, CA (US)

(73) Assignee: CareFusion 202, Inc., San Diego, CA (US)

( * ) Notice: Subject to any disclaimer, the term of this patent is extended or adjusted under 35 U.S.C. 154(b) by 320 days.

(21) Appl. No.: 17/321,348

(22) Filed: May 14, 2021

(65) Prior Publication Data

US 2021/0369956 A1 Dec. 2, 2021

Related U.S. Application Data

(60) Provisional application No. 63/030,232, filed on May 26, 2020.

(51) Int. Cl.
| | | |
|---|---|---|
| *A61M 5/142* | (2006.01) | |
| *A61M 5/165* | (2006.01) | |
| *A61M 5/168* | (2006.01) | |

(52) U.S. Cl.
CPC ........ *A61M 5/14248* (2013.01); *A61M 5/165* (2013.01); *A61M 5/16881* (2013.01); *A61M 2005/14252* (2013.01)

(58) Field of Classification Search
CPC .......... A61M 5/16813; A61M 5/14244; A61M 5/152; A61M 5/16877
See application file for complete search history.

(56) References Cited

U.S. PATENT DOCUMENTS 5,084,021 A * 1/1992 Baldwin ............. A61M 5/1424
604/131
5,167,631 A * 12/1992 Thompson ............ A61M 5/152
222/386.5

(Continued)

FOREIGN PATENT DOCUMENTS

| AU | 640083 B2 | 8/1993 |
| AU | 654796 B2 | 11/1994 |

(Continued)

OTHER PUBLICATIONS

International Search Report and Written Opinion for Application No. PCT/US2021/033483, dated Sep. 6, 2021, 15 pages.

(Continued)

*Primary Examiner* — Laura A Bouchelle
(74) *Attorney, Agent, or Firm* — Morgan, Lewis & Bockius LLP

(57) ABSTRACT

Methods and systems for infusing a user. An infusion pump includes a housing with an elastic component configured to expand and store potential energy. The infusion pump includes a first tube fluidically coupled to an outlet of the housing. The first tube is configured to conduct the fluid from the housing at a first flow rate. The infusion pump includes an air filter fluidically coupled to a distal end of the first tube via an air filter inlet. The infusion pump includes a second tube fluidically coupled to the air filter via an air filter outlet. The second tube is configured to adjust the first flow rate of the fluid conducted from the housing to a second flow rate. The infusion pump further includes one or more components for distributing the fluid to a user, the one or more components fluidically coupled to an outlet of the second tube.

17 Claims, 10 Drawing Sheets

(56) References Cited

U.S. PATENT DOCUMENTS

| | | | |
|---|---|---|---|
| D339,193 S | 9/1993 | Thompson et al. | |
| 5,290,238 A * | 3/1994 | Crass | A61M 5/152 604/246 |
| 5,356,379 A | 10/1994 | Vaillancourt | |
| 5,368,570 A | 11/1994 | Thompson et al. | |
| 5,419,770 A | 5/1995 | Crass et al. | |
| 6,562,000 B2 | 5/2003 | Thompson et al. | |
| 6,595,950 B1 | 7/2003 | Miles et al. | |
| 6,645,183 B2 | 11/2003 | Christensen et al. | |
| 6,685,670 B2 | 2/2004 | Miles et al. | |
| 6,923,785 B2 | 8/2005 | Miles et al. | |
| 6,979,311 B2 | 12/2005 | Miles et al. | |
| 7,341,572 B2 * | 3/2008 | Bridle | A61M 5/152 604/153 |
| 7,766,860 B2 * | 8/2010 | Olsen | A61M 25/0029 604/246 |
| 7,892,213 B2 | 2/2011 | Walborn | |
| 8,323,246 B2 * | 12/2012 | Chiravuri | A61M 5/1723 604/132 |
| 10,420,886 B2 * | 9/2019 | Sealfon | G06Q 50/22 |
| 2005/0245867 A1 | 11/2005 | Olsen et al. | |
| 2011/0098673 A1 | 4/2011 | Walborn | |

FOREIGN PATENT DOCUMENTS

| | | |
|---|---|---|
| CA | 2068701 C | 1/1995 |
| WO | WO-2016140864 A1 | 9/2016 |

OTHER PUBLICATIONS

U.S. Government Accountability Office, "Medicare: CMS Should Evaluate Providing Coverage for Disposable Medical Devices That Could Substitute for Durable Medical Equipment", U.S. Government Accountability Office, GAO-17-600, Published Jul. 17, 2017, retrieved at https://www.gao.gov/products/gao-17-600.

* cited by examiner

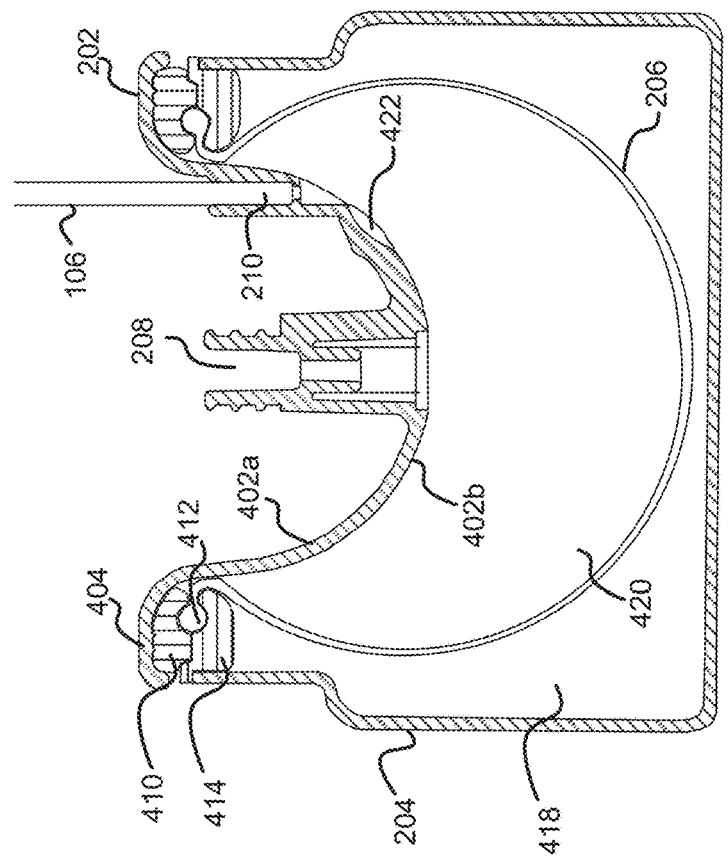
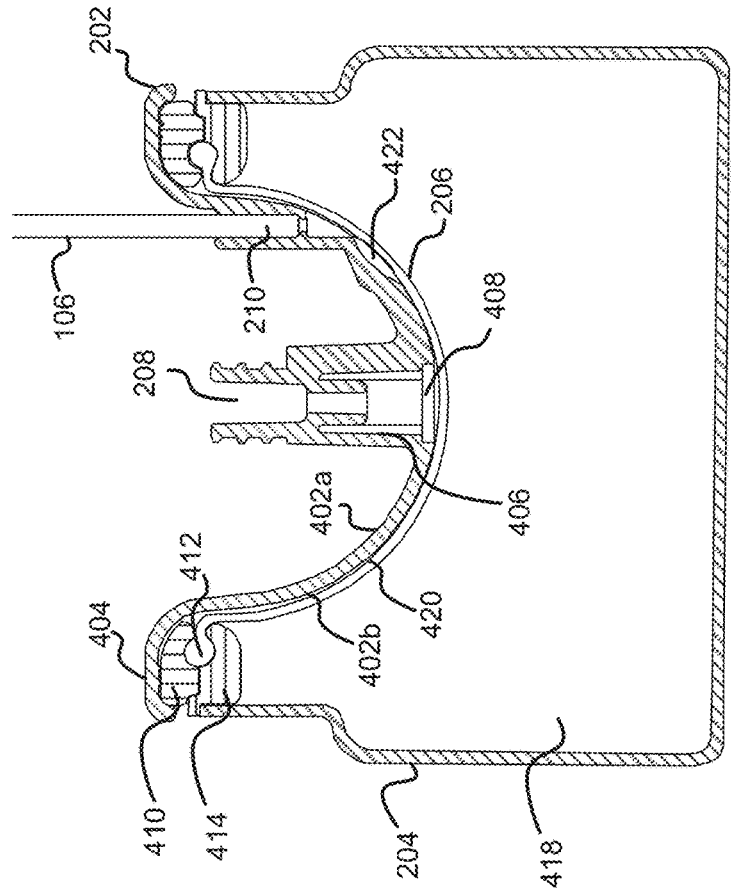

800

802
Expand the elastic component with the fluid to store potential energy generated by the fluid within the infusion pump

804
The elastic component includes an elastomeric membrane

806
The membrane is a single layer of silicon

808
The elastic component is configured to expand hold a volume of at least 50 mL

810
The elastic component is configured to expand hold a volume of at least 100 mL

812
The elastic component is configured to expand hold a volume of at least 250 mL

814
The elastic component is formed of a single layer membrane and the housing includes an inlet for receiving the fluid, and the method further receives the fluid via the inlet; and expands the elastic component and generating the potential energy stored by the elastic component based on the fluid received via the inlet

816
Conduct, from the first tube, fluid from the housing at a first flow rate based, in part, on the potential energy stored by the elastic component

818
The first flow rate is further based, at least in part, on an inner diameter of the first tube

820
The first flow rate is further based, at least in part, on a length of the first tube

Figure 8A 800 (Cont.)

822-a
The infusion pump further includes an external flow restrictor coupled to an exterior potion of the first tube, and the infusion pump configure to:

822-b
Provide, via the external flow restrictor, an external pressure to the first tube that closes a fluid passageway of the first tube

822-c
Remove, via the external flow restrictor, the external pressure from the first tube that opens the fluid passageway of the first tube

824
Expel air from the fluid via the one or more air vents of the air filter, the air expelled substantially upstream such that the fluid exiting the air filter is primed without air

826
The air filter includes a membrane filter, and the infusion pump removes one or more contaminants and particulates from the fluid

828
Adjust the first flow rate of the fluid conducted from the housing, via the first tube, to a second flow rate, the second flow rate based, at least in part, on an inner diameter of the second tube

830
The inner diameter of the second tube is no greater than 0.0075 inches

832
The second tube is a predetermined length, and the second flow rate is further based on the predetermined length

834
An inner diameter of the first tube and the inner diameter of the second tube are the same

836
An inner diameter of the first tube and the inner diameter of the second tube are distinct

Figure 8B 800 (Cont.)

826 (Cont.)

838
The second flow rate is no greater than 5ml/hr

840
The second flow rate is about 2 mL/hr

842
Distribute the fluid to a user via one or more components fluidically coupled to the outlet of the second tube segment

844
The outlet of the second tube segment is a fixed male luer

846
The one or more components configured to connect with the outlet of the second tube include a skin patch, a needle, a cannula, and a catheter

848
The infusion pump includes a flow restrictor component within the first tube, the flow restrictor component having a diameter less than an inner diameter of the first tube

850
The diameter of the flow restrictor component greater than a diameter of the inlet and/ or outlet of the air filter, and/or the distal outlet

852
The flow restrictor component is unfixed within the first tube and configured to move a length of the first tube

854
The flow restrictor component is fixed within the first tube and configured to remain at a predetermined location of the first tube

Figure 8C 800 (Cont.)

846 (Cont.)

856
The flow restrictor component is a pin configured to change the shape of the fluid from a cylindrical shape to a torus shape

858
The pin has a predetermined radius, and the first flow rate is further based, in part, on the radius of the pin

860
The pin has a predetermined length, and the first flow rate is further based, in part, on the predetermined length of the pin

862
The pin is made of glass or metal

864
The flow restrictor component is one or more rigid beads that are configured to have the fluid move around a diameter of the one or more rigid beads, wherein the first flow rate is further based, in part, on the diameter of the one or more rigid beads, and the one or more rigid beads do not cause the first tube to expand while the fluid move around the diameter of the one or more rigid beads

866
The one or more beads can be variable in size

868
At least two rigid beads are included in the first tube

870
The one or more rigid beads are made of glass or metal

872
The infusion pump further includes a controller chip, and the infusion pump operates a valve to control the first flow rate of the fluid

874
The controller chip is controlled via USB

876
The controller chip is controlled wirelessly

878
The controller chip includes firmware to automatically control the flow rate

Figure 8D

INFUSION PUMP FLOW RATE CONTROL

CROSS REFERENCE TO RELATED APPLICATIONS

This application claims the benefit of U.S. Provisional Application Ser. No. 63/030,232, entitled "INFUSION PUMP FLOW RATE CONTROL," filed on May 26, 2020, the entirety of which is incorporated herein by reference.

TECHNICAL FIELD

The present disclosure pertains to fluid pumps. More particularly, portable infusion pumps which are useful for pumping relatively small amounts of fluids under substantially constant pressure at accurate and constant flow rates over a sustained period of time. The present invention is particularly, but not exclusively, useful for a one-time use as a disposable pump for infusing fluid medicaments to an ambulatory patient.

BACKGROUND

Disposable pumps (also called elastomeric pumps, ambulatory pumps or CADD pumps) have been around for some time. These disposable pumps offer distinct low-cost care advantages and are used in a variety of applications from antibiotic administration, pain management, up to and including chemotherapy administration. Alternate site care (e.g., at home or in mass oncology clinics) is also becoming more common. Given the rising costs of healthcare, more non-acute options are needed. Disposable pumps are able to provide users with a cost effective way meet their healthcare needs. However, current disposable pumps are not always able to provide accurate and consistent flow rates to infuse fluid medicament to a user.

Hence, those skilled in the art have recognized a need for disposable pumps that are able to provide users with fluid medicament at an accurate and constant flow rate. Yet a further identified need is for a flow restrictor that can be manufactured more cost effectively and can use interchangeable parts with restrictors of differing sizes. The invention fulfills these needs and others.

SUMMARY

In some implementations, an infusion pump includes a housing. The housing includes an elastic component configured to expand and store potential energy generated by the fluid within the infusion pump. The infusion pump includes a first tube fluidically coupled to an outlet of the housing. The first tube is configured to conduct the fluid from the housing at a first flow rate based, in part, on the potential energy stored by the elastic component. The infusion pump includes an air filter fluidically coupled to a distal end of the first tube via an air filter inlet. The air filter configured to expel air from the fluid, via one or more air vents, substantially upstream such that the fluid exiting the air filter is primed without air. The infusion pump includes a second tube fluidically coupled to the air filter via an air filter outlet that is configured to adjust the first flow rate of the fluid conducted from the housing, via the first tube, to a second flow rate. The second flow rate is based, at least in part, on an inner diameter of the second tub. The infusion pump further includes an outlet of the second tube fluidically coupled to one or more components for distributing the fluid to a user.

In some implementations, a method of infusing fluid to a patient is performed at an infusion pump. The infusion pump includes a housing that includes an elastic component, a first tube fluidically coupled to the housing, via an outlet of the housing, an air filter fluidically coupled to a distal end of the first tube via an air filter inlet, a second tube fluidically coupled to the air filter via an air filter outlet, and an outlet of the second tube fluidically coupled to one or more components. In some implementations, the method performed at the infusion pump includes expanding the elastic component with the fluid to store potential energy generated by the fluid within the infusion pump; conducting, from the first tube, fluid from the housing at a first flow rate based, in part, on the potential energy stored by the elastic component; expelling air from the fluid via the one or more air vents of the air filter, where the air is expelled substantially upstream such that the fluid exiting the air filter is primed without air; adjusting the first flow rate of the fluid conducted from the housing, via the first tube, to a second flow rate, the second flow rate based, at least in part, on an inner diameter of the second tube; and distributing the fluid to a user via the one or more components coupled to the outlet of the second tube.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIGS. 4A and 4B illustrate cross sectional views of the disposable pump, in accordance with some implementations.

FIGS. 8A-8D are flowcharts illustrating a method for controlling the flow rate of the disposable pump, according to some implementations

DETAILED DESCRIPTION

Implementations as disclosed herein include an infusion pump and infusion methods for infusing a user with fluid medicament. The infusion pump is coupled to a user and configured to provide the fluid medicament to the user with an accurate and constant flow rate. Accordingly, implementations as disclosed herein provide different devices and/or techniques for controlling and/or adjusting the flow rate of the fluid medicament. In addition, by providing the fluid medicament to a user with accurate and constant flow rates that can be controlled, the infusion pump and infusion methods, as disclosed herein, facilitate the safe infusion of fluid medicament.

Some additional advantages of the implementations consistent with the present disclosure include precise control of the flow rates and lower achievable flow rates for fluid medicament distributed to a user. In particular, the infusion pump can be designed to produce the desired flow rate and, if needed, can finely tune the flow rate as needed. Further, the infusion pump and the infusion methods allow for great flexibility in achieving different flow rates by using one or more of the techniques and/or devices disclosed herein. Implementations as disclosed herein are suitable for a variety of fluid medicaments and/or applications (e.g., chemotherapy administration, antibiotic administration, pain management, etc.). Accordingly, improving the flexibility in adjusting the flow rates and/or increasing the number of applications of the infusible pumps reduces the total costs by provided an affordable alternative for fluid medicament infusion that is functional across a variety of applications.

Figure 1:
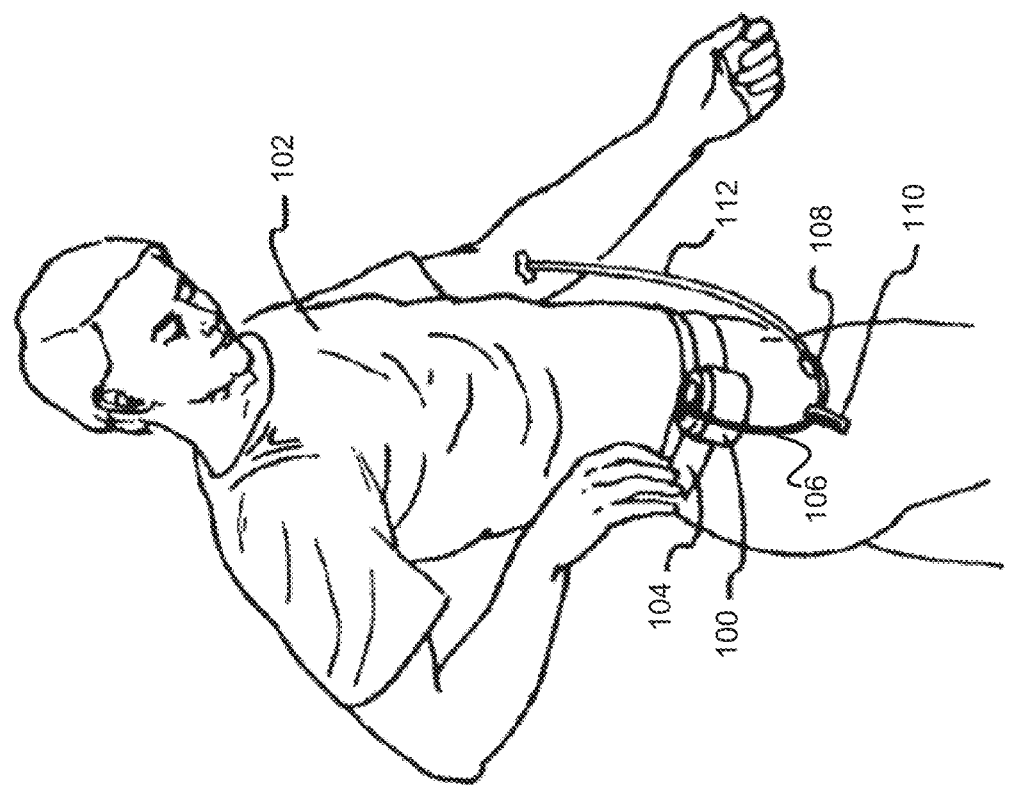
FIG. 1 illustrates a disposable infusion pump, in accordance with some implementations.

FIG. 1 illustrates a disposable infusion pump in accordance with some implementations. As indicated in FIG. 1, the disposable pump 100 (also referred to herein as an infusion pump) may be worn by a user 102 during ambulation and can be attached to the user 102 by holder 104. The holder 104 can be a belt, a fanny pack, a lanyard, a backpack, a pouch, and/or other device for carrying the disposable pump 100. Further, FIG. 1 shows that the disposable infusion pump 100 can be fluidically coupled to the user 102 for the infusion of fluids into the user 102 through a first medical tubing 106. In some implementations, the fluid can be water or any fluid medicament such as chemotherapy drugs, pain drugs, prescription drugs, saline, etc. The first medical tubing 106 can be any type of IV tubing for infusion tubing, such as air filtered micro-bore IV tubing, small-bore IV tubing, large-bore IV tubing, and/or any other type of tubing for infusion.

In some implementations, the material for the first medical tubing 106 is Tygon®, thermoplastic elastomers (TPE), polyethylene, polyvinyl chloride (PVC), nylon, silicone, and/or other similar material. The Tygon material bonds to the various components of the infusion pump using a single solvent application. Tygon material may provide an advantage in that it can be extruded at a significantly smaller inner diameter than other types of tubing (e.g., PVC) on the pump, and improve flow rate accuracy, and may make the tubing much less sensitive to length adjustments. In addition, a small change in diameter accuracy may have an exponential impact on rate accuracy.

In some implementations, an in-line air filter 108 is fluidically coupled to the first medical tubing 106 (via an inlet of the in-line air filter 108). The in-line air filter 108 can be a pediatric filter IV filter, a micro IV filter, and/or other suitable filters for drug delivery, chemotherapy, insulin infusion, antibiotic therapy Lipid/TPN infusion, neonatal infusion therapy, etc. The in-line air filter 108 is configured to remove air from the conducted fluid (e.g., leaving the disposable pump 100) in order to prevent the infusion of air to the user 102. In some implementations, the in-line air filter 108 is configure to remove contaminants and/or particles from the fluid to prevent the infusion of harmful substance to the user 102. In some implementations, the air filter is located near the disposable pump 100 (as described below) such that air is expelled from the fluid substantially upstream and the fluid exiting the air filter is primed (without air) for user 102 infusion. Primed, in some implementations, means filling the medical tubing 106 with fluid so that it is ready to be infused into the user 102.

In some implementations, a second medical tubing 112 is fluidically coupled to the in-line air filter 108 (via an outlet of the in-line air filter 108). In some implementations, the first medical tubing 106 and the second medical tubing 112 are the same (e.g., same type of tubing (e.g., material), size (e.g., inner and outer diameter) of tubing, length of tubing, etc.). In some other implementations, the first medical tubing 106 and the second medical tubing 112 are distinct (e.g., with one or more variations in the type of tubing, size (e.g., inner and/or outer diameter) of tubing, length of tubing, etc.). The first medical tubing 106 and the second medical tubing 112 are discussed in further detail below with reference to FIGS. 4A-4B.

Additionally or alternatively, in some implementations, an external flow restrictor 110 is coupled to the first medical tubing 106 (e.g., via an exterior portion of the first medical tubing 106) to provide and/or remove an external pressure to the first medical tubing 106. The external pressure to the first medical tubing 106 is configured to close or open a fluid passageway of the first medical tubing 106 (e.g., stop or start the flow of fluid from the pump 100 by applying enough pressure to the first medical tubing 106 to act as a shut-off valve). The external flow control 110 can be a slide clamp, a pinch clamp, a roller clamp, a screw clamp, and/or any other type of device capable of initiating or terminating the flow of fluid from the disposable pump 100.

Figure 2:
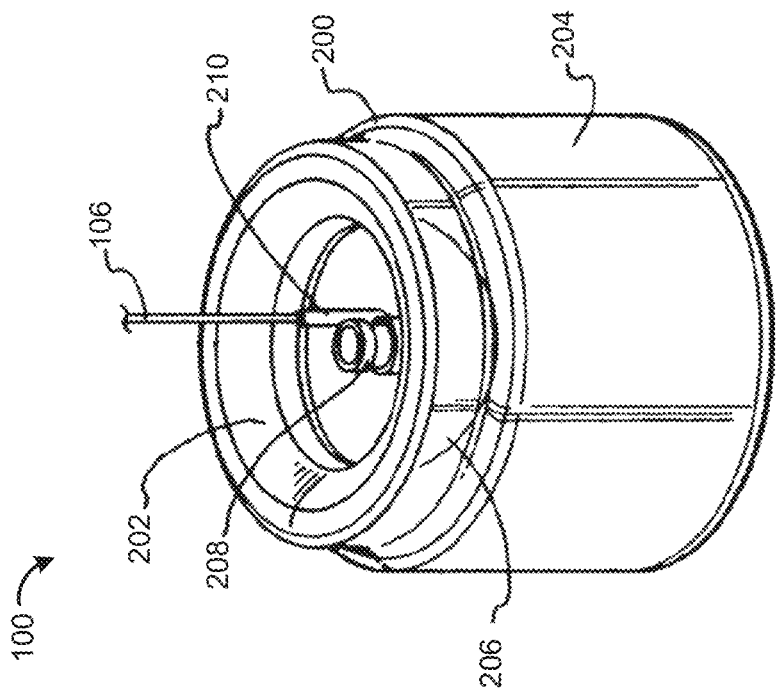
FIG. 2 illustrates a disposable infusion pump, in accordance with some implementations.

FIG. 2 illustrates an overview of the disposable infusion pump 100 in accordance with some implementations. In some implementations, the disposable pump 100 includes a housing 200, which is an assembly of a first portion 202 and a second portion 204. In some implementations, the first portion 202 includes a first surface 402a (e.g., an exterior or upper surface; shown in FIG. 4) and a second surface 402b directly opposite the first surface (e.g., an internal or bottom surface (when the first portion 202 and the second portion 204 are coupled); shown in FIG. 4). In some implementations, the first surface of the first portion 202 includes an inlet 208 and an outlet 210 for receiving and distributing fluids, respectively. In some implementations, the second surface includes an elastic component 206 coupled between a first ring 410 and a second ring 414 (shown in FIG. 4). The first and second rings are affixed to the second surface. In particular, in some implementations, the first ring is affixed to the second surface via, edges 404 of the first portion (e.g., shown in FIG. 4). The elastic component 206, as discussed below, is configured to expand and store potential energy generated by the fluid within the infusion pump. As further shown in FIG. 2, in some implementations, the first medical tubing 106 is coupled to the outlet 210 (on the first surface) of first portion 202 such that fluid can be distributed from the disposable pump 100 (when loaded with fluid as described below in reference to FIG. 4).

Figure 3:
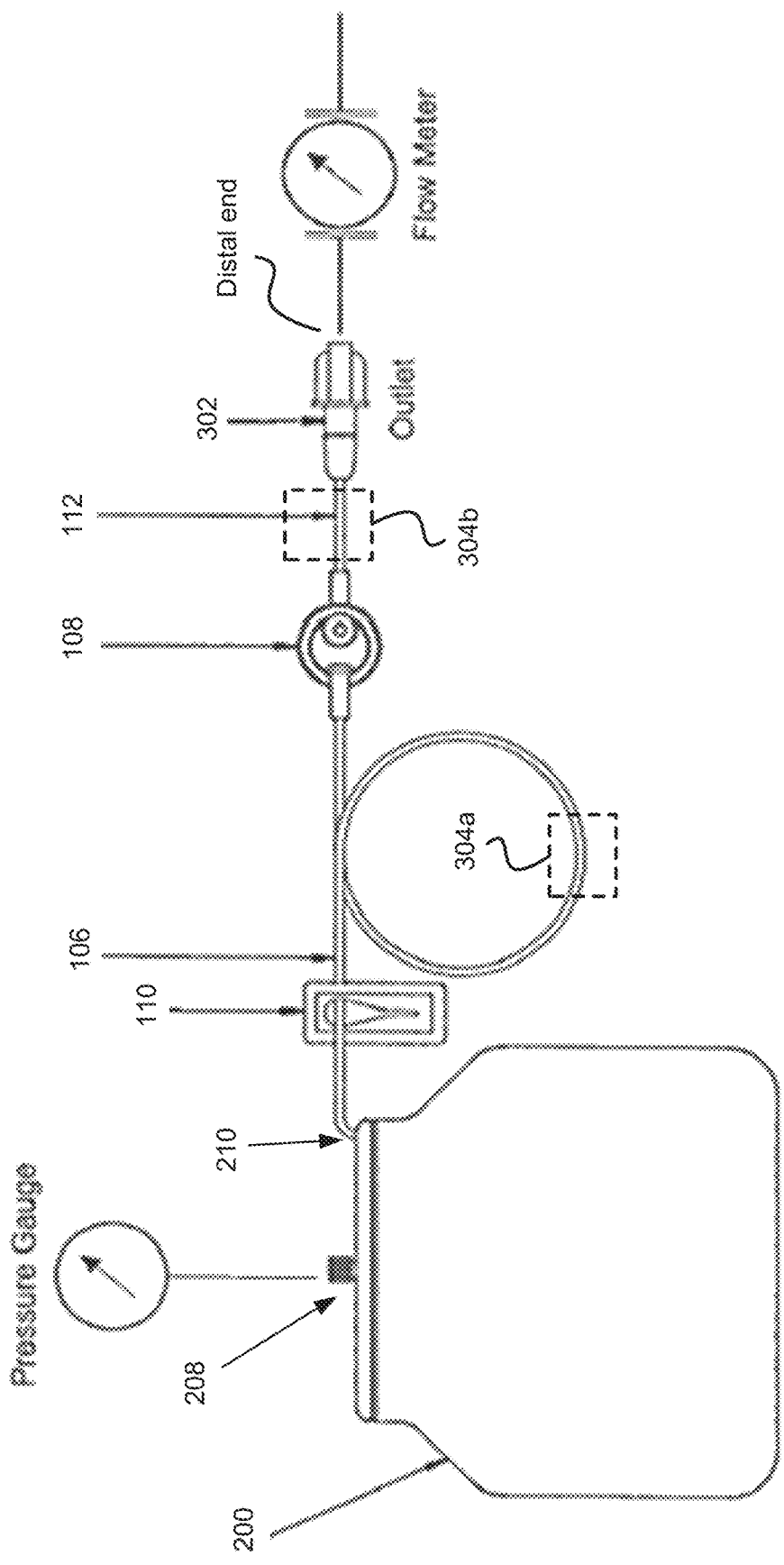
FIG. 3 is an overview of the disposable pump system, in accordance with some implementations.

FIG. 3 is an overview of a pump system in accordance with some implementations. In some implementations, the first portion 202 (including a first 402a and second 402b surface; shown in FIG. 4) of housing 200 is made of a hard plastic, such as polycarbonate and/or other materials that are chemically compatible with the fluid to be infused to the user 102. In some implementations, the first portion 202 has a parabolic (or dome/diaphragm shape) with the second surface 402b extending in a direction opposite first surface 402a (e.g., the first surface being indented slightly). In some implementations, the first portion 202 is configured to stretch the elastic component 206 (via the second surface 402b) into a similar shape when assembled (e.g., as shown in FIGS. 4A and 4B). In some implementations, the second surface 402b of the first portion 202 defines the shape of the elastic component 206 (e.g., while storing potential energy or not). In some implementations, edges 404 of the first portion 202 extend outwardly from the second surface 402b to provide a surface to couple the elastic component 206 onto the first portion 202 (e.g., via the upper 410 and lower 414 rings as described below). As will be appreciated by one of ordinary skill in the art, the first portion 202 of housing 200 can be manufactured using injection molding, urethane casting, 3D molding, and/or other manufacturing procedures.

In some implementations, a valve sleeve 406 and a valve insert 408 are inserted into inlet 208 (e.g., the valve sleeve 406 and the valve insert 408 shown in FIG. 4). When inserted into inlet 208, the sleeve 406 and valve insert 408 generate a one-way valve for the first portion 202 of housing 200 that permits the flow of fluid in one direction (e.g., externally through the inlet 208). An important aspect of the disposable pump 100 is to be able to fill the disposable pump 100 with fluid through the inlet 208 and to secure the fluid such that the fluid is not able to leave the disposable pump 100 (e.g., exit through the inlet 208 and/or other portions of housing 200). In some implementations, a fluid is loaded into the inlet 208 under pressure utilizing a syringe (not shown) or other device for injecting a fluid.

In some implementations, the disposable pump 100 includes at least two retainer rings (e.g., an upper ring 410 and a lower ring 414). In some implementations, the upper ring 410 is engaged with a rib 412 that defines the elastic component 206 (e.g., rib 412 shown in FIG. 4). In some implementations, the upper ring 410 is also configured to be engaged with the lower ring 414 effectively coupling the rib 412 of the elastic member 206 between the upper ring 410 and lower ring 414. The upper ring 410 and the lower ring 414 can be of any suitable rigid material such as polycarbonate. The upper ring 410 and the lower ring 414 when joined together support the elastic component 206, and provide a firm foundation for the elastic component 206 to expand and store potential energy as described below with respect to FIGS. 4A and 4B.

In some implementations, the elastic component 206 is a substantially circular and planar when it is not expanded (e.g., in a relaxed and/or unstretched state). As described above, rib 412 defines the shape of the elastic component 206 (e.g., in a relaxed or pressurized state) and is configured to be coupled between the upper ring 410 and lower ring 414. Traditionally, elastic component 206 is composed of multiple layers of elastomeric material with at least one layer of multiple layers acting as a drug barrier. The multiple layers of the elastic component 206 are used to hold the fluid medicament. A drug barrier is a layer that protects the fluid (held by the multiple layers of the elastic component 206) from contamination from other layers or the multiple layers. The drug barrier, however, does not always prevent chemical leaching that occurred because of the material of the other layers of the multiple layers. Chemical leeching is the movement of contaminants and/or other water-soluble particulates into the fluid medicament. The material of the elastomeric material include natural rubber, isoprene, silicon and/or other material having a high elastic memory (e.g., material that is able to expand and is naturally or automatically configured to return to its relaxed state).

To solve the leeching problem, in some implementations, the elastic component 206 is composed of a single layer. In some implementations, the single layer is liquid injection molded silicone. In some implementations, the elastomeric material of the elastic component 206 is uniform thickness. In some implementations, the elastomeric material of the elastic component 206 can include a thickness that varies across the elastic component 206 (so long as the elastic component 206 is able to expand and store potential energy). The varying thickness can strengthen portions of the elastic component 206 experiencing larger loads (e.g., higher loads on edges of the elastic component 206, near the rib 412, when fluid is loaded in disposable pump 100).

In some implementations, disposable pump 100 includes a second portion 204 of housing 200. The second portion 204 can be ajar, a bottle, and/or any other container with a shape that has an opening for receiving the first portion 202 of housing 200 including the elastic component 206. In some implementations, the second portion 204 is made of a hard or semi-rigid plastic, such as a PETG, that can be manufactured with processes such as blow molding and/or similar processes. In some other implementations, the second portion 204 is made of glass. The elastic component 206 and disposable pump 100 can be of various sizes, and the second portion 204 can be sized accordingly. For example, the second portion 204 can have an opening 416 large enough to fit the elastic component 206 and/or other components described herein, such as the at least two retainer rings. Similarly, the second portion 204 is configured to contain (e.g., enclose) the elastic component 206 when fully expanded. In some other implementations, the size for second portion 204 can be made compatible with the proposed maximum fluid capacity for the disposable pump 100 (as discussed below).

In some implementations, fluid (e.g., fluid medicament) that is loaded into the disposable pump 100 via the inlet 208 is configured to deliver from outlet 210 via the first medical tubing 106. The first medical tubing 106, conducts the fluid from the housing 200 at a first flow rate. The first flow rate is based, at least in part, on the potential energy stored by the by the elastic component 206 when it is expanded by the fluid loaded into the inlet 208 (e.g., via a syringe or other similar device). In some implementations, the first flow rate is based on the inner diameter of the first medical tubing 106, the length of the first medical tubing 106, and/or other factors (e.g., viscosity of the fluid, temperature, changes in pressure, etc.). In some implementations, the first flow rate is configured to rapidly prime the infusion system for delivery of the fluid to the user 102. In some implementations, the first flow rate is selected based on the second flow rate (as discussed below) to account for increase in the total time needed to prime the disposable pump 100. In other words, the first flow rate can be selected to rapidly prime the disposable pump 100 while the second flow rate is configured to provide the fluid medicament to the user 102 with the appropriate (e.g., selected) flow rate. In some implementations, the first flow rate is no greater than 167 mL/hr (+/−0.25 mL/hr). In some implementations, the first flow rate is between the 5 mL/hr and 167 mL/hr. In some other implementations, finer control of the first flow rate is achievable reaching a flow rate less than 5 mL/hr (e.g., flow rates of about 2 mL/hr+/−0.25 mL/hr). In some implementations, control of the first flow rate can be achieved by adjusting the diameter and/or length of the first medical tubing 106. Different methods of controlling the flow rate are discussed below.

In some implementations, an external flow restrictor 110 is coupled to an exterior portion of the first medical tubing 106. The external flow restrictor 110 is configured to provide or remove an external pressure to the first medical tubing 106 that respectively closes or opens a fluid passageway of the first medical tubing 106. In other words, in some implementations, the external flow restrictor 110 blocks the flow of liquid medicament leaving the housing 200 (e.g., fluid leaving via outlet 210). In some implementations, external flow restrictor 110 blocks the fluid passageway of the first medical tubing 106 such that fluid injected via the inlet 208 expands the elastic component 206 (e.g., the disposable pump 100 can be loaded without distributing the fluids before enough potential energy is stored). In some implementations, the elastic component 206, when expanded, stores potential energy that is used to create a pressure difference to infuse the user 102. As such, the external flow restrictor 110 or similar device is needed to create enough potential energy to ensure that the disposable pump 100 creates a substantial constant fluid pumping pressure when the elastic component 206 contracts from an expanded state to a relaxed state. It should be noted that the fluid injected into disposable pump 100, via the inlet 208, needs to be loaded with sufficient energy to overcome the resistance of the elastic component 206. In some implementations, a medical syringe and/or any other tool for injecting fluid can be used to overcome the resistance of the elastic component 206. Additional information about the elastic component 206 is discussed below in FIGS. 4A and 4B.

In some implementations, an in-line air filter 108 is included in the infusion system. In some implementations, the air filter 108 is fluidically coupled to a distal end of the first medical tubing 106 (e.g., the end of the first medical tubing 106 opposite the outlet 210), via an air filter inlet. The air filter 108 is located substantially upstream near the outlet 210. In some implementations, the air filter 108 configured to expel air from the fluid via one or more air vents. The air is expelled substantially upstream such that the fluid exiting the air filter 108 is primed without air. In some implementations, the air filter 108 includes a membrane filter that is configured to remove one or more contaminants and particulates from the fluid.

In some implementations, second medical tubing 112 is fluidically coupled to the air filter 108 via an air filter outlet. The second medical tubing 112 is configured to adjust the first flow rate of the fluid conducted from the housing 200, via the first medical tubing 106, to a second flow rate. The second flow rate based, at least in part, on an inner diameter of the second medical tubing 112. In some other implementations, the second flow rate is based on the length of the first medical tubing 106, and/or other factors (e.g., viscosity of the fluid, temperature, changes in pressure, etc.). In some implementations, the first flow rate and the second flow rate are selected to quickly prime disposable pump 100. For example, the first flow rate may be selected to be significantly higher than the second flow rate such that the disposable device is substantially primed leaving only a smaller portion of the disposable pump 100 to be primed (e.g., the first flow rate may prime ¾ of the disposable pump 100 (such as the length of the first medical tubing 106 and air filter 108) leaving only ¼ to be primed at the second flow rate (such as the length of the second medical tubing 112)). In some implementations, the second flow rate is no greater than 5 mL/hr. In some implementations, the second flow rate is between the 2 mL/hr and 5 mL/hr. In some other implementations, the second flow rate is about 2 mL/hr (e.g., about being +/−0.25 mL/hr). In some implementations finer control of the second flow rate (e.g., lower than 2 mL/hr) can be achieved by adjusting the diameter and/or length of the second medical tubing 112. In some implementations, the inner diameter of the second medical tubing 112 is no greater than 0.0075 inches. In some implementations, the second medical tubing 112 is a predetermined length that is dependent on the targeted flow rate (e.g., a longer length generates a slower flow rate). In some embodiments, the second medical tubing 112 is used adjust the flow rate of the fluid medicament before it is distributed to the user 102.

As mentioned above in FIG. 1, the inner diameter of the first medical tubing 106 and the inner diameter of the second medical tubing 112 can be the same or distinct. Similarly, in some implementations, the length, the material, and/or other parameters of the first medical tubing 106 and the second medical tubing 112 can be the same or distinct. The parameters for the first medical tubing 106 and the second medical tubing 112 depend on the flow rate that needed to infuse the user 102. The second medical tubing 112 is used to achieve the desired flow rate before the fluid is infused to user 102.

In some implementations, an outlet 302 of the second medical tubing 112 (e.g., a distal outlet) is fluidically coupled to the second medical tubing 112. The outlet 302 of the second medical tubing 112 is configured connect with one or more components for distributing the fluid to a user 102. In some implementations, the outlet 302 of the second medical tubing 112 is a fixed male luer. In some implementations, the one or more components configured to connect with the outlet 302 of the second medical tubing 112 include a skin patch, a needle, a cannula, and a catheter and/or other components for infusing the user 102.

In some implementations, a flow restrictor component is placed within the first medical tubing 106 and/or the second medical tubing 112. For example, the flow restrictor component can be located at a first location 304a within the first medical tubing 106 and/or at a second location 304b within the second medical tubing 112. In some implementations, the flow restrictor can be placed at each location (e.g., the first 304a and second 304b location). The flow restrictor component can be placed at any location within the first medical tubing 106 and/or the second medical tubing 112. For example, the flow restrictor component can be placed adjacent to the outlet 210 of the housing 200 (e.g., within the first medical tubing 106), adjacent to an outlet 302 of the second medical tubing 112, adjacent to the inlet or outlet of the air filter 108, and/or anywhere in between. In some implementations, the flow restrictor component is unfixed and configured move freely along the first medical tubing 106 and/or the second medical tubing 112. Alternatively or additionally, in some implementations, the flow restrictor component is fixed (anchored or fastened) at a particular location of the first medical tubing 106 and/or the second medical tubing 112 (e.g., such that the flow restrictor component does not move).

The flow restrictor component is independent of the flow control provided by the first medical tubing 106 and/or the second medical tubing 112. In some implementations, the flow restrictor component includes one or more pins and/or beads as described below in FIGS. 5A-6B. The flow restrictor component has a diameter less than an inner diameter of the first medical tubing 106 and/or the second medical tubing 112. In some implementations, the flow restrictor component has a diameter greater than the inlet and/or outlet of the air filter 108 such that the flow restrictor component stays within a particular location or portion of the tube (e.g., within the first medical tubing 106 or the second medical tubing 112). In some implementations, the flow restrictor component has a diameter greater than the outlet 302 of the second medical tubing 112 such that the flow restrictor component does not flow into the user 102. Further, the flow restrictor component is configured not to break or come apart as a user moves the first medical tubing 106 and/or the second medical tubing 112. The flow restrictor component is discussed in more detail in FIGS. 5 and 6.

In some implementations, the disposable pump 100 includes a controller chip (not shown) configured to operate a valve to control the first flow rate and/or the second flow rate of the fluid. The controller chip is discussed below in FIG. 7. In some implementations, the controller chip is a discrete component fluidically coupled i-line with one or more components of the disposable pump 100. For example, the controller chip can be fluidically coupled to the between the outlet 210 of disposable pump 100 and the first medical tubing 106; the first medical tubing 106 and the air filter 108; the air filter 108 and the second medical tubing 112; and/or second medical tubing 112 and the outlet 302 of the second medical tubing 112. Alternatively or additionally, in some implementations the controller chip is coupled to the housing 200. The flow controller chip is discussed in more detail in reference to FIG. 7.

FIGS. 4A and 4B illustrate cross sectional views of the disposable pump 100, in accordance with some implementations. More specifically, FIGS. 4A and 4B illustrate the expansion of the elastic component 206 as fluid is introduced through the inlet 208 of housing 200 and into the fluid storage 420 (which stores potential energy generated by expanded elastic component 206) under the pressure of a syringe, or some other tool for pumping a fluid. In some implementations, air in the system is removed (e.g., vented) via outlet 210 along the indentation 422, which is formed based on the second surface 402b.

FIG. 4A shows upper ring 410 coupled with lower ring 414, and rib 412 coupled in between the two. As mentioned above, rib 412 defines the shape of elastic component 206. In some implementations, the upper ring 410 and lower ring 414 are coupled by ultrasonic welding and/or solvent bonding. In some implementations, the upper ring 410 is coupled to the first portion 202 (e.g., via edges 404) and the lower ring 414 is coupled to the second portion 204 using ultrasonic welding or solvent bonding. The elastic component 206 is positioned across the opening 416 of second portion 204 and creates cavity 418 (e.g., a space created within housing 200). In some implementations, when the first portion 202 and the second portion 204 of housing 200 are coupled together (via the upper 410 and lower rings 414), the second surface 402b of the first portion 202 stretches elastic component 206 in the shape of the second surface 402b (e.g., as shown in FIG. 4). In some implementations, the dimensions of both the elastic component 206 and the second surface 402b are such that the elastic component 206 is stretched to a state where its elasticity does not behave in a linear fashion. In particular, the elastic component 206 is stretched to a state where changes in the stress of the material of the elastic component 206 are not linearly proportional to changes in the strain of the material during the operation of the disposable pump 100.

FIG. 4B show a cross section view of disposable pump 100 after fluid has been injected via inlet 208 of the first portion 202 of housing 200, in accordance with some implementations. In some implementations, the injected fluid expands elastic component 206 to create expanded fluid storage 420. Expanded fluid storage 420 is under the pressure of a syringe and/or other too that is used to inject fluid (via inlet 208) into disposable pump 100 (after air has been removed from the system via the outlet (via inlet 210) along the indentation 422, which is formed based on the second surface 402b. As mentioned above, an external flow restrictor 110 can be used to block a fluid passageway of the first medical tubing 106 such that fluid does not leave outlet 210 allowing for the fluid storage 420 to expand as fluid is injected into the disposable pump 100. In order to create a substantially constant fluid pumping pressure in the fluid storage 420, the expansion and subsequent contraction of elastic component 206 is achieved when, before fluid is injected in inlet 208, the elastic component 206 is stretched to a state where its elasticity is nonlinear. As mentioned above, this state is achieved by the shape and/or dimensions of the second surface 402b and/or the elastic component 206 during assembly of the housing 200. It should be noted that the medical syringe (not shown) and/or any other tool used to inject fluid into the disposable pump 100 must inject the fluid with enough force to overcome the current state the elastic component 206 (e.g., enough force to overcome the force generated by the elastic component 206 to contract). The elastic component 206 must be stretched non-linearly to form and expand the fluid storage 420 as shown in FIG. 4B.

In some implementations, the fluid storage 420 is configured to expand to hold a volume of at least 50 mL of fluid. In some other implementations, the fluid storage 420 is configured to expand to hold a volume of at least 100 mL of fluid. In yet other implementations, the fluid storage 420 is configured to expand to hold a volume of at least 250 mL of fluid.

In general, a fluid must be introduced under a pressure sufficient to overcome the potential energy of the initially stretched elastic component 206 (stretched by the second surface 402b). Similarly, a fluid must be introduced under a pressure that is sufficient to further stretch (non-linearly) the elastic component 206 and form the fluid storage 420. The potential energy stored by the fluid storage 420 is the total amount of energy available for discharging the fluid (e.g., out of outlet 210). The fluid storage 420, even after fully discharging the fluid, has residual potential energy due to the elastic component 206 being stretch over the second surface 402b.

The flow of fluid through the first medical tubing 106 and/or the second medical tubing 112 can be characterized by the Hagen-Poiseuille equation. The flow can be characterized by the Hagen-Poiseuille equation because it is assumed that the flow through the first medical tubing 106 and/or the second medical tubing 112 is laminar flow. Further, because of the characteristics of the elastic component 206 (e.g., elastomeric material that applies constant pressure on the stored fluids), the pressure generated by the disposable pump 100 (P_device) is considered to be constant. At the same time, it is assumed that that the pressure generated by the patient (P_patient) is also effectively constant. With these assumptions, the following Hagen-Poiseuille equation can be used to define the flow of the fluid from the disposable pump 100 to user 102:

$$P\_device - P\_patient = flowrate * (restrictor\ resistance)$$

This equation can be further characterized as $$V = \frac{\Delta p \pi D^4}{128 \mu L},$$

where:
V=velocity of fluid flow;
D=the diameter of the flow restrictor conduit;
Δp=energy loss (i.e. pressure change over a length L);
L=length of flow restrictor; and
μ=fluid viscosity.

According to the Hagen-Poiseuille equation, if there is a constant energy loss over the length of a tube (as assumed in the present implementations), then a constant flow rate of fluid through a tube can be achieved (e.g., by designing the first medical tubing 106 and/or the second medical tubing 112 as described herein). It can be assumed that there is constant energy loss over the length of a tube (e.g., the first medical tubing 106 and/or the second medical tubing 112) because, as mentioned above, P_device and P_patient are considered to be constant. As a practical matter, P_patient is negligibly small. As such, the flow of disposable pump 100 is due almost entirely to the constant pressure produced by the stored potential energy of the elastic member 206.

In other words, to determine a specific value for the flow rate of fluid from disposable pump 100 through the first medical tubing 106 and/or the second medical tubing 112 to user 102, the P_device and the physical design of the first medical tubing 106 and/or the second medical tubing 112 must be consideration together. In particular, the pressure held by the elastic component 206 (e.g., stored potential energy) is used along with the respective diameter and/or length of the first medical tubing 106 and/or the second medical tubing 112 to determine the flow rate for the disposable pump 100.

Figure 5A:
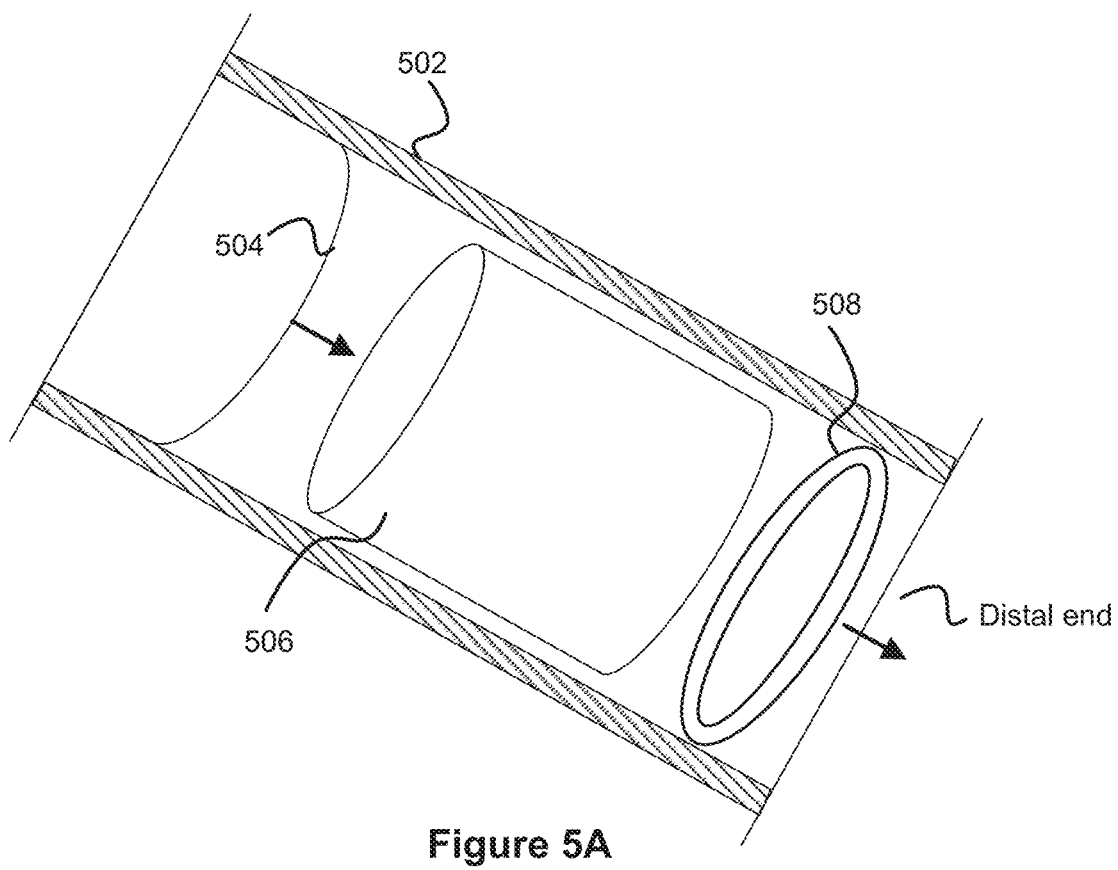
FIGS. 5A and 5B illustrate a flow restrictor component, in accordance with some implementations.
Figure 5B:
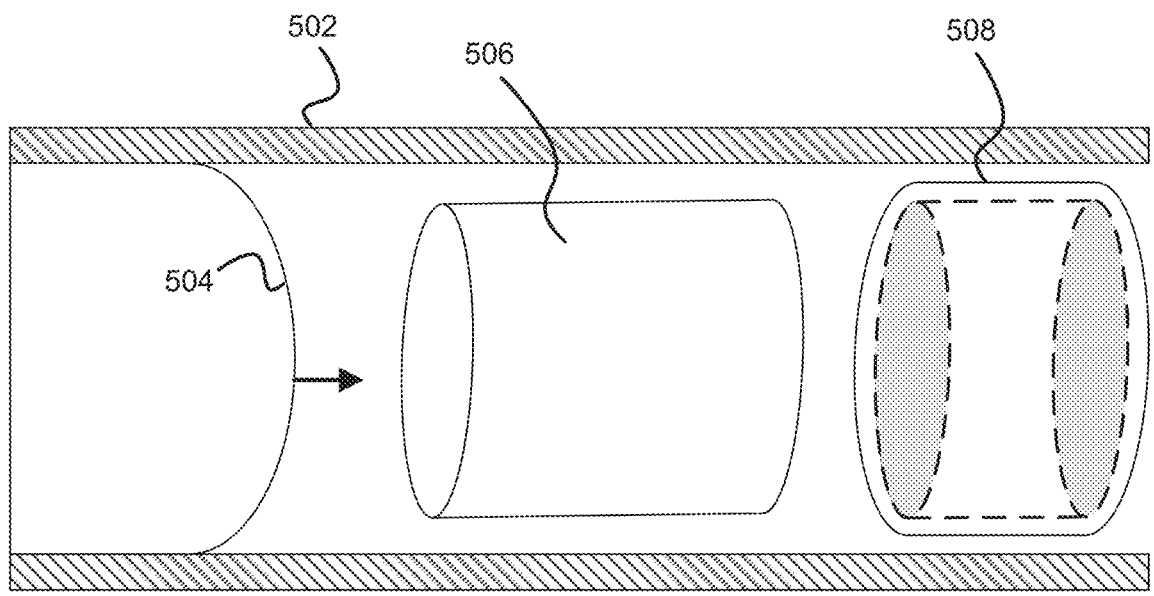

FIGS. 5A and 5B illustrate a flow restrictor component in accordance with some implementations. In FIG. 5A, a tube segment 502 (e.g., either the first medical tubing 106 and/or the second medical tubing 112) including a flow restrictor component, such as a pin 506, is shown. In some implementations, the pin 506 has a diameter less than the inner diameter of the tube segment 502 such that the pin 506 can be located within the tube segment 502. In some implementations, the pin 506 has a diameter greater than the inlet and/or outlet of the air filter 108 and/or the outlet 302 of the second medical tubing 112. In this way, the pin 506 remains within the tube segment 502 without moving between different tube segments (e.g., from the first medical tubing 106 to the second medical tubing 112 and vice versa) and/or to prevent the pin 506 from being infused to user 102. In some implementations, the pin 506 is fixed (anchored at a particular location) or unfixed (moveable along a length) within the tube segment 502. In some implementations, the pin 506 has a predetermined length. In some implementations, the pin 506 is made of glass or metal.

In some implementations, the pin 506 is configured to adjust (e.g., decrease) the flow rate (e.g., either the first flow rate or the second flow rate as discussed above in FIG. 3). In some implementations, adjustment of the flow rate is based, in part, on the diameter of the pin 506. In some implementations, the pin 506 is configured to change the shape of the fluid from a cylindrical shape (e.g., cylindrical flow 504) to a torus shape (e.g., doughnut or torus flow 508). For example, as show in FIG. 5A, the pin 506 changes the cylindrical flow 504 to a torus flow 508 where the radius of the torus flow 508 is based, in part, on the diameter of the pin 506. Although the torus flow 508 is shown as a single ring, it should be noted that torus flow 508 is a continuous stream (as shown in FIG. 5B). In some implementations, the change in the flow rate shape decreases the flow rate by disrupting the flow and having the flow move around the pin 506 (e.g., without causing the tube segment 502 to expand or change shape). In some implementations, the flow rate is further based, in part, on the predetermined length of the pin 506.

FIG. 5B shows a partial cross-sectional side view of the flow restrictor component in FIG. 5A. As shown in FIG. 5B, cylindrical flow 504 flows from the disposable pump 100 (e.g., via outlet 210) towards the distal end (end opposite outlet 210 of disposable pump 100) of the tube segment 502. In some implementations, the pin 506 reduces the flow rate of the cylindrical flow 504 by reducing the cross sectional area of the cylindrical flow 504 by the cross sectional area of the pin 506, and, thus, changing the flow to a torus flow 508. In particular, the area of the cylindrical area of the tube segment 502 is reduced by the cross sectional area of the pin 506. In some implementations, the pin 506 generates an annular section (e.g., the length of pin 506) within the tube segment 502. The flow within the annular section of the tube segment 502 follows the following Poiseuille equation:

$$Q = \frac{G\pi}{8\mu}\left[R_2^4 - R_1^4 - \frac{(R_2^4 - R_1^4)^2}{\ln\frac{R_2}{R_A}}\right],$$

where:
Q=flow rate;
$R_1$=the radius of the pin 506;
$R_2$=the radius of the tube segment 502;
G=the change in pressure over the length; and
μ=fluid viscosity.

As mentioned above, it can be assumed that the change in the pressure is constant over the length of a tube (e.g., the first medical tubing 106 and/or the second medical tubing 112) because P_device and P_patient are considered to be constant. Using the above equation, a constant flow rate of fluid through a tube segment 502 with pin 506 can be achieved (e.g., by designing the first medical tubing 106, the second medical tubing 112, and/or the pin 506 as described herein). In other words, to determine a specific flow rate for the fluid from disposable pump 100 through the first medical tubing 106 and/or the second medical tubing 112 with a pin 506, the P_device and the physical design of the first medical tubing 106, the second medical tubing 112, and/or the pin 506 must be consideration together. In particular, the pressure held by the elastic component 206 (e.g., stored potential energy) is used along with the respective diameter of the first medical tubing 106, the second medical tubing 112, and/or the pin 506 to determine the flow rate for the disposable pump 100. As a practical matter, P_patient is negligibly small. As such, the flow of disposable pump 100 is due almost entirely to the constant pressure produced by the stored potential energy of the elastic member 206.

Figure 6A:
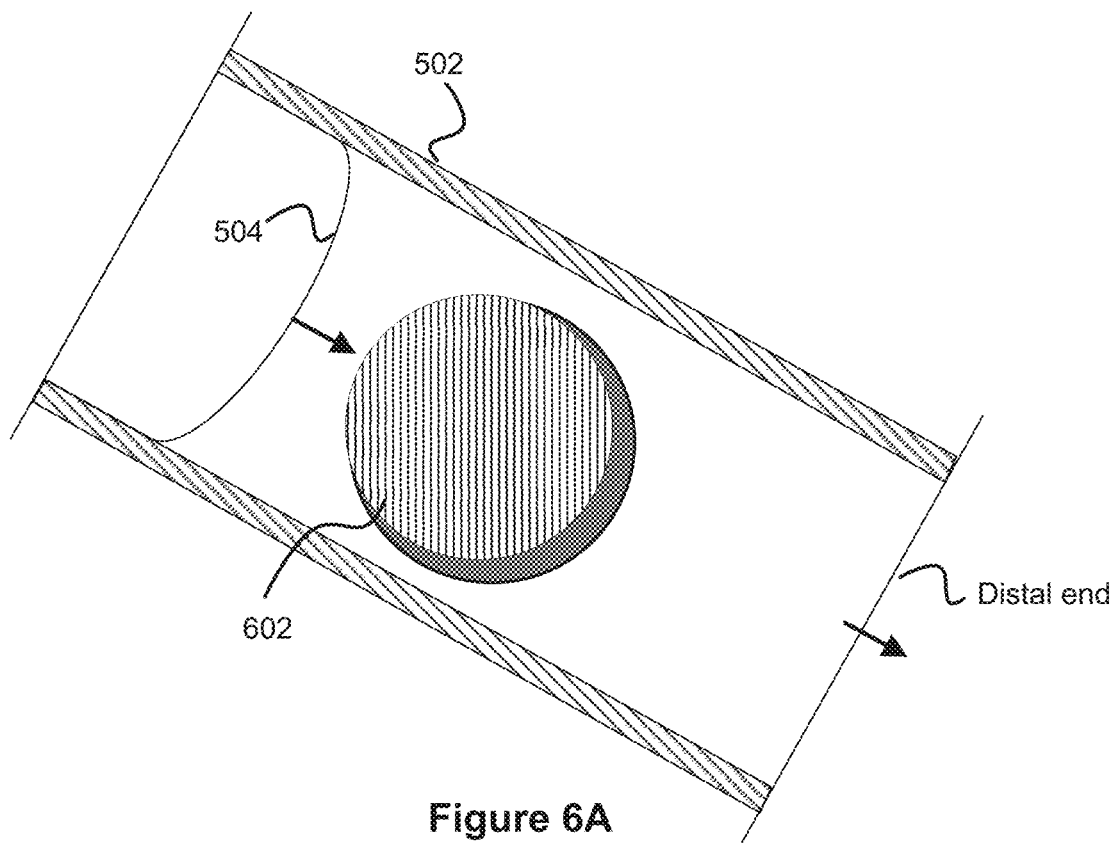
FIGS. 6A and 6B illustrate another flow restrictor component, in accordance with some implementations.
Figure 6B:
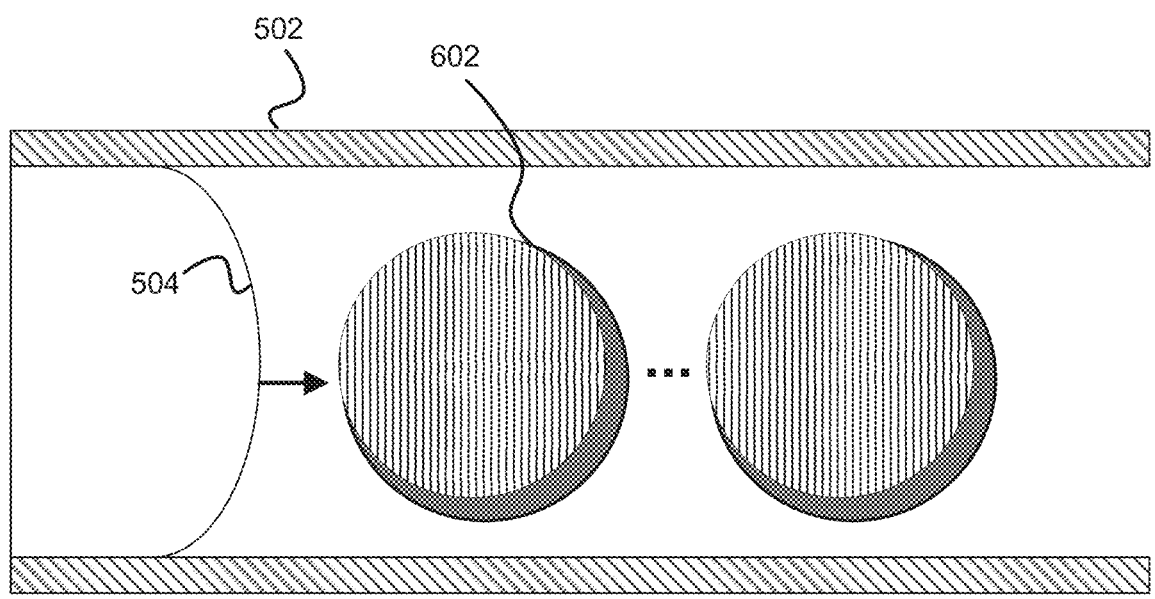

FIGS. 6A and 6B illustrate another flow restrictor component in accordance with some implementations. In FIG. 6A, a tube segment 502 (e.g., either the first medical tubing 106 and/or the second medical tubing 112) including another flow restrictor component, such as one or more rigid beads 602, is shown. In some implementations, the one or more rigid beads 602 have a diameter less than the inner diameter of the tube segment 502 such that the one or more rigid beads 602 can be located within the tube segment 502.

In some implementations, the one or more rigid beads 602 have a diameter greater than the inlet and/or outlet of the air filter 108 and/or the outlet 302 of the second medical tubing 112. In this way, the one or more rigid beads 602 remain within the tube segment 502 without moving between different tube segments (e.g., from the first medical tubing 106 to the second medical tubing 112 and vice versa) and/or to prevent the one or more rigid beads 602 from being infused to user 102. In some implementations, the one or more rigid beads 602 are fixed (anchored) or unfixed (moveable) within the tube segment 502. In some implementations, each rigid bead of the one or more rigid beads 602 is the same. In some other implementations, at least one rigid bead (or all) of the one or more rigid beads 602 can be distinct carrying in size (e.g., the one or more rigid beads 602 have varying diameters).

In some implementations, the rigid beads 602 may be made of glass or metal. According to various aspects, the rigid beads may be sized so that placement of the rigid beads does not cause the tubing (e.g., tube segment 502) to expand.

As mentioned above, in some implementations, the one or more rigid beads 602 have a diameter less than the inner dimeter of the tube segment 502. In this regard, a flow rate through tubing segment may be defined, at least in part, by a function of the cross-sectional area or diameter of the bead(s) within the tubing, the difference between the cross-sectional area or diameter of the bead and the inner diameter of the tubing, and/or the number of the beads within the tubing or their collective mass within a predetermined area of the tube segment 502.

In some implementations, the one or more rigid beads 602 are configured to adjust (e.g., decrease) the flow rate (e.g., either the first flow rate or the second flow rate as discussed above in FIG. 3). In some implementations, adjustment of the flow rate is based, in part, on the diameter of the one or more rigid beads 602. In particular, the one or more rigid beads 602 are configured to have the fluid (e.g., cylindrical flow 504) move around their surface or diameter (e.g., without causing the tube segment 502 to expand or change shape). The flow rate is based, in part, on the diameter of the one or more rigid beads (e.g., the area that the fluid needs to move around). In some implementations, the flow rate is further based on the number of one or more rigid beads 602 within the tube segment 502 (e.g., each rigid bead of the one or more rigid beads 602 decreasing the flow rate).

FIG. 6B shows a partial cross-sectional side view of the flow restrictor component in FIG. 6A. As shown in FIG. 6B, at least two rigid beads of the one or more rigid beads 602 are within the tube segment 502. Further shown in FIG. 6B is cylindrical flow 504 flowing from the disposable pump 100 (e.g., via outlet 210) towards the distal end (end opposite outlet 210 of disposable pump 100) of the tube segment 502. In some implementations, the one or more rigid beads 602 reduce the flow rate of the cylindrical flow 504 by reducing the cross sectional area of the cylindrical flow 504 by the cross sectional area of the one or more rigid beads 602. In particular, the area of the cylindrical area of the tube segment 502 is reduced by the cross sectional area of the one or more rigid beads 602. In some implementations, the flow within the tube segment 502 with the one or more rigid beads 602 follows the Poiseuille equations as described above (e.g., derived for the respective diameters and/or circumference of the one or more rigid beads 602).

As mentioned above in FIGS. 5A and 5B, it can be assumed that the change in the pressure is constant over the length of a tube (e.g., the first medical tubing 106 and/or the second medical tubing 112) because P_device and P_patient are considered to be constant. Using the Poiseuille equations, a constant flow rate of fluid through a tube segment 502 with the one or more rigid beads 602 can be achieved (e.g. by designing the first medical tubing 106, the second medical tubing 112, and/or the one or more rigid beads 602 as described herein). In other words, to determine a specific flow rate for the fluid from disposable pump 100 through the first medical tubing 106 and/or the second medical tubing 112 with the one or more rigid beads 602, the P_device and the physical design of the first medical tubing 106, the second medical tubing 112, and/or the one or more rigid beads 602 must be consideration together. In particular, the pressure held by the elastic component 206 (e.g., stored potential energy) is used along with the respective diameter of the first medical tubing 106, the second medical tubing 112, and/or the one or more rigid beads 602 to determine the flow rate for the disposable pump 100. As a practical matter, P_patient is negligibly small. As such, the flow of disposable pump 100 is due almost entirely to the constant pressure produced by the stored potential energy of the elastic member 206.

In some implementations, the different flow restrictor components can be combined in the tube segment 502. For example, in some implementations, the tube segment 502 can include pin 506 and one or more rigid beads 602.

Figure 7:
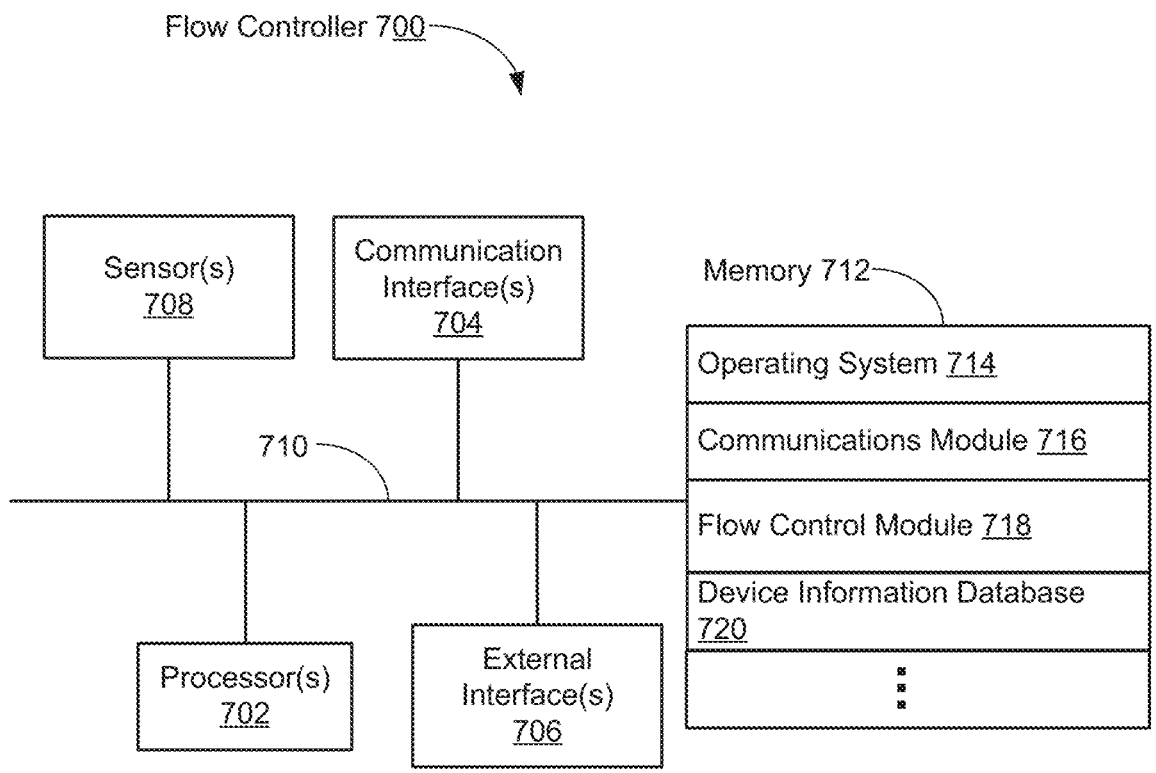
FIG. 7 is a block diagram depicting a flow controller, in accordance with some implementations.

FIG. 7 is a block diagram depicting a flow controller 700 in accordance with some implementations. In some implementations, the disposable pump 100 includes a flow controller 700 that is configured to control the flow of fluid discharged from the disposable pump 100. In some implementations, the flow controller 700 is coupled to the housing (e.g., via the first 202 and/or second portion 202 of the housing 200). Alternatively, in some implementations, the flow controller 700 is fluidically coupled in-line with the first medical tubing 106, the second medical tubing 112, and/or other components of the disposable pump 100 (e.g., between the first medical tubing 106 and the outlet 210, the first medical tubing 106 and the air filter 108, etc.). In some implementations, the flow controller 700 operates one or more pillows (e.g., expandable components to block a fluid passageway), a valve, and/or similar components to control the available fluid passageway of the disposable pump 100 and select a desired flow rate. In some implementations, the one or more pillows, the valve, and/or the similar components are placed adjacent (e.g., wither before or after) to the outlet 210 of disposable pump 100. In some implementations, the flow controller 700 (including the one or more pillows, the valve, and/or the similar components) is a discrete component fluidically coupled in-line with one or more components of the disposable pump 100 (e.g., such that the fluid enters an inlet of the flow controller 700 at a first flow rate and exits an outlet of the flow controller 700 at a second flow rate selected by the user 102). Additionally or alternatively, in some implementations, the one or more pillows, the valve, and/or the similar components are placed with the first medical tubing 106 and/or the second medical tubing 112. The flow rate controller 700 is configured to achieve a selected flow rate as low as 0.48 ml/hr.

The flow controller 700 includes one or more processing units (including, e.g., a processor, processor core, or other type of controller chip) 702, one or more network or other communications interfaces 704 (e.g., one or more antennas), memory 712, one or more sensors 708, and one or more communication buses 710 for interconnecting these components. The communication buses 710 optionally include circuitry (sometimes called a chipset) that interconnects and controls communications between system components. In some implementations, the flow controller 700 may include external interfaces 706 for manually controlling the flow controller 700. In some implementations, the one or more external interfaces 706 of the flow controller 700 may include, for example, input devices such as a keyboard, a mouse, touch sensitive surfaces and/or controllers, a trackpad, USB and/or USB devices, and/or input buttons. In some implementations, the sensors 708 are used to collect data on the flow rate, the pressure held within the elastic component 206 (e.g., fluid storage 420), and/or other information needed to determine the flow rate of the disposable pump 100. The one or more components of the flow controller 700 are sterilized to prevent contamination of the fluid medicament. Similarly, the one or more components of the flow controller 700 are separated from the flow passageway of the disposable pump 100 (with the exception of the one or more pillows, the valve, and/or the similar components) to further prevent contamination and/or to prevent the fluid from damaging the flow controller 700.

The memory 712 may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 712 includes one or more storage devices remotely located from the processor(s) 702. The memory 712, or alternatively the non-volatile memory device(s) within the memory 712, includes a non-transitory computer-readable storage medium. In some implementations, the memory 712 or the computer-readable storage medium of the memory 712 stores programs, modules, and/or data structures that may be used for the performing one or more operations of the flow controller 700. For example, the memory 712 may include programs, modules, and/or data structures for an operating system 714, a network communication module 716, a flow control module 718, and device information database 720.

In some implementations, the operating system 714 module may include procedures for handling various basic system services and for performing hardware dependent tasks. The network communication module 716 may be configured for connecting the flow controller 700 to other computing devices via the one or more communication network interfaces 704 (wired or wireless) and one or more communication networks, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link, a WLANS connection, or other wireless connection. The flow control module 718 is configured to adjust the flow rate as desired. In some implementations, the flow control module 718 determines the flow rate using the Hagen-Poiseuille equations described above. In particular, the flow control module 718 can determine the flow rate using data collected from the one or more sensors 708 and the device information database 720. In some implementations, the flow control module 718 is configured to operate automatically (e.g., firmware designed to reach and/or maintain a desired flow rate). Alternatively or additionally, in some implementations, flow controller 700 and the flow control module 718 can be manually operated by a user 102 via the external interfaces 706 and/or the communications interfaces 704 (e.g., receiving wireless controls from a remote device such as a laptop, computer, mobile phone, tablet, etc.). In some implementations, the disposable pump 100 can be controlled via a dedication application. The device information database 720 includes data for the disposable pump 100 such as the length of the first medical tubing 106 and/or the second medical tubing 112, the diameter of the first medical tubing 106 and/or the second medical tubing 112, the maximum capacity of the elastic component 206, the pressure (e.g., potential energy) stored by the elastic component 206 while loaded with different amounts of fluid, viscosity of one or more different types of fluids, and/or other useful information.

FIGS. 8A-8D are flowcharts illustrating a method 800 for controlling the flow rate of the disposable pump 100 according to some implementations. Method 800 may be performed at a disposable pump 100, the disposable pump 100 comprising, at least, a housing 200 including an elastic component 206 The disposable pump 100 further comprises, at least, a first tube (e.g., first medical tubing 106) fluidically coupled to the housing 200 via an outlet 210; an air filter 108 fluidically coupled to a distal end of the first tube (e.g., first medical tubing 106) via an air filter inlet; a second tube (e.g., second medical tubing 112) fluidically coupled to the air filter 108 via an air filter outlet; and an outlet 302 of the second medical tubing 112 fluidically coupled to the second tube. In some implementations, the housing 200 includes a first portion 202 that includes a first 402a and second 402b surface, the first surface 402a includes the outlet 210 for distributing the fluid, and the second surface 402b, opposite the first surface 402a. In some implementations, the elastic component 206 is coupled between a first ring 410 and a second ring 414. The first ring 410 and the second ring 414 is affixed to the second surface 402b. In some implementations, the disposable pump 100 further comprises, at least, a second portion 204 that is configured to house the second surface 402b of the first portion 202, the first portion 202 and the second portion 204 are coupled.

Methods consistent with the present disclosure may include at least some, but not all, of the operations illustrated in method 800, performed in a different sequence. Furthermore, methods consistent with the present disclosure may include at least two or more steps as in method 800 performed overlapping in time, or almost simultaneously.

The method 800 includes expanding (802) the elastic component 206 with the fluid to store potential energy generated by the fluid within the infusion pump 100. In some implementations, the elastic component includes (804) an elastomeric membrane. In some implementations, the membrane is (806) a single layer of silicon. In some implementations, the elastic component 206 is configured to expand (808) hold a volume of at least 50 mL. In some implementations, the elastic component 206 is configured to expand (810) hold a volume of at least 100 mL. In some implementations, the elastic component 206 in configured to expand (812) hold a volume of at least 250 mL.

In some implementations, the elastic component is formed of a single layer membrane and the housing 200 (of the infusion pump) includes an inlet 208 for receiving the fluid, and method 800 includes receiving (814) the fluid via the inlet; and expanding the elastic component 206 and generating the potential energy stored by the elastic component 206 based on the fluid received via the inlet.

Method 800 includes conducting (816), from the first tube (e.g., the first medical tubing 106), fluid from the housing 200 at a first flow rate based, in part, on the potential energy stored by the elastic component 206. In some implementations, the first flow rate is further based (818), at least in part, on an inner diameter of the first tube. In some implementations, the first flow rate is further based (820), at least in part, on a length of the first tube. Determinations of the flow rates are based on the potential energy stored by the elastic component 206 and the Hagen-Poiseuille equations as described above in FIGS. 4A-6B.

In some implementations, the infusion pump further includes (822-a) an external flow restrictor 110 coupled to an exterior portion of the first tube, and method 800 incudes, at the infusion pump, providing (822-b), via the external flow restrictor 110, an external pressure to the first tube that closes a fluid passageway of the first tube. In some implementations, method 800 incudes removing (822-c), via the external flow restrictor 110, the external pressure from the first tube that opens the fluid passageway of the first tube. As described above in FIGS. 4A and 4B, the external flow restrictor 110 can be used to load (e.g., inject fluid) the elastic component 206 (e.g., expanding the elastic component 206 to create fluid storage 420).

Method 800 includes expelling (824) air from the fluid via the one or more air vents of the air filter 108. The air is expelled substantially upstream such that the fluid exiting the air filter is primed without air. In some implementations, the air filter includes (826) a membrane filter, and method 800 includes, at the infusion pump, removing one or more contaminants and particulates from the fluid.

Method 800 includes adjusting (828) the first flow rate of the fluid conducted from the housing 200, via the first tube, to a second flow rate, the second flow rate based, at least in part, on an inner diameter of the second tube (e.g., second medical tubing 112). In some implementations, the inner diameter of the second tube is (830) no greater than 0.0075 inches. In some implementations, the second tube is (832) a predetermined length, and the second flow rate is further based on the predetermined length. In some implementations, an inner diameter of the first tube and the inner diameter of the second tube are (834) the same. In some implementations, an inner diameter of the first tube and the inner diameter of the second tube are (836) distinct. In some implementations, the second flow rate is (838) no greater than 5 mL/hr. In some other implementations, the second flow rate is (840) about 2 mL/hr (about, in some implementations, means+/−0.2 mL/hr). Determinations of the flow rates are based on the potential energy stored by the elastic component 206 and the Hagen-Poiseuille equations as described above in FIGS. 4A-6B.

Method 800 includes distributing (842) the fluid to a user 102 via one or more components fluidically coupled to the outlet 302 of the second medical tubing 112. In some implementations, the outlet 302 of the second medical tubing 112 is (844) a fixed male luer. In some implementations, the one or more components configured to connect with the outlet 302 of the second medical tubing 112 include (846) a skin patch, a needle, a cannula, and a catheter.

In some implementations, the infusion pump includes (848) a flow restrictor component (e.g., pin 506 and/or rigid beads 602) within the first tube, the flow restrictor component having a diameter less than an inner diameter of the first tube. In some implementations, the diameter of the flow restrictor component is (850) greater than a diameter of the inlet and/or outlet of the air filter 108, and/or the outlet 302 of the second medical tubing 112. This way, the flow restrictor component remains within a particular tube segment and/or is not infused in user 102 (as described above in FIGS. 5A-6B). In some implementations, the flow restrictor component is (852) unfixed within the first tube. In some other implementations, the flow restrictor component is (854) fixed within the first tube. Although the example provided herein has the flow restrictor component in the first tube, it should be noted that the flow restrictor component could be in the second tube and/or both the first and second tube.

In some implementations, the flow restrictor component is (856) a pin 506 configured to change the shape of the fluid from a cylindrical shape (e.g., cylindrical flow 504) to a torus shape (e.g., torus flow 508). In some implementations, the pin 506 has (858) a predetermined radius, and the first flow rate is further based, in part, on the radius of the pin 506. In some implementations, the pin 506 has (860) a predetermined length, and the first flow rate is further based, in part, on the predetermined length of the pin. The effects of the pin 506 on the flow are discussed above in reference to FIGS. 5A and 5B. In some implementations, the pin 506 is (862) made of glass or metal.

In some other implementations, the flow restrictor component is (864) one or more rigid beads that are configured to have the fluid move around a diameter of the one or more rigid beads, the first flow rate is further based, in part, on the diameter of the one or more rigid beads, and the one or more rigid beads do not cause the first tube to expand while the fluid move around the diameter of the one or more rigid beads. In some implementations, the one or more rigid beads can be (866) variable in size. In particular, all of the rigid beads can be the same (having the same diameters) or distinct (having varying diameters between rigid beads). The effects of the one or more rigid beads 602 on the flow are discussed above in reference to FIGS. 6A and 6B. In some implementations, at least two rigid beads are (868) included in the first tube. In some implementations, the one or more rigid beads are (870) made of glass or metal.

In some implementations, the infusion pump further includes a controller chip (e.g., flow controller 700), and method 800, at the infusion pump, operates (872) a valve to control the first flow rate of the fluid. In some implementations, the controller chip is controlled (874) via a USB. In some other implementations, the controller chip is controlled (876) wirelessly (e.g., via wireless protocols, such as Bluetooth, or a dedicated application). In some implementations, the controller chip includes (878) firmware to automatically control the flow rate. The flow rate controller 700 is controlled to achieve a selected flow rate (e.g., as low as 0.48 ml/hr). In some implementations, the one or more components of the flow controller 700 (e.g. wireless component 704, the external interfaces 706, sensors 708, etc.) are sterilized and separated from the fluid passageway such that the fluid medicament is not contaminated. The flow controller 700 is discussed in detail above in reference to FIG. 7.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An infusion pump comprising: a housing including an elastic component configured to expand and store potential energy generated by the fluid within the infusion pump, and a first tube fluidically coupled to an outlet of the housing, the first tube configured to conduct the fluid from the housing at a first flow rate based, in part, on the potential energy stored by the elastic component; an air filter fluidically coupled to a distal end of the first tube via an air filter inlet, the air filter configured to expel air from the fluid via one or more air vents, wherein the air is expelled substantially upstream such that the fluid exiting the air filter is primed without air; a second tube fluidically coupled to the air filter via an air filter outlet, wherein: the second tube configured to adjust the first flow rate of the fluid conducted from the housing, via the first tube, to a second flow rate, the second flow rate based, at least in part, on an inner diameter of the second tube, and an outlet of the second tube is configured to fluidically couple to one or more components for distributing the fluid to a user.

Clause 2. The infusion pump of Clause 1, wherein the inner diameter of the second tube is no greater than 0.0075 inches.

Clause 3. The infusion pump of any of the proceeding Clauses, the second tube is a predetermined length, and the second flow rate is further based on the predetermined length.

Clause 4. The infusion pump of any of the proceeding Clauses, wherein an inner diameter of the first tube and the inner diameter of the second tube are the same.

Clause 5. The infusion pump of any of Clauses 1 through 3, wherein an inner diameter of the first tube and the inner diameter of the second tube are distinct.

Clause 6. The infusion pump of any of the proceeding Clauses, further comprising a flow restrictor component within the first tube, wherein the flow restrictor component has a diameter less than an inner diameter of the first tube.

Clause 7. The infusion pump of Clause 6, wherein the flow restrictor component is a pin configured to change the shape of the fluid from a cylindrical shape to a torus shape, wherein: the pin has a predetermined radius, and the first flow rate is further based, in part, on the predetermined radius of the pin.

Clause 8. The infusion pump of any of Clauses 6 and 7, wherein the flow restrictor component is a pin configured to change the shape of the fluid from a cylindrical shape to a torus shape, wherein: the pin has a predetermined length, and the first flow rate is further based, in part, on the predetermined length of the pin.

Clause 9. The infusion pump of any of Clauses 6 through 8, wherein the flow restrictor component is one or more rigid beads that are configured to have the fluid move around a diameter of the one or more rigid beads, wherein: the first flow rate is further based, in part, on the diameter of the one or more rigid beads, and the one or more rigid beads do not cause the first tube to expand while the fluid move around the diameter of the one or more rigid beads.

Clause 10. The infusion pump of Clause 9, wherein at least two rigid beads are included in the first tube.

Clause 11. The infusion pump of any of Clauses 6 through 10, wherein the flow restrictor component is unfixed within the first tube and configured to move a length of the first tube.

Clause 12. The infusion pump of any of Clauses 6 through 10, wherein the flow restrictor component is fixed within the first tube and configured to remain at a predetermined location of the first tube Clause 13. The infusion pump of any of the proceeding Clauses, wherein the outlet of the second tube is a fixed male luer.

Clause 14. The infusion pump of any of the proceeding Clauses, wherein the air filter includes a membrane filter that is configured to remove one or more contaminants and particulates from the fluid.

Clause 15. The infusion pump of any of the proceeding Clauses, further comprising an external flow restrictor coupled to an exterior portion of the first tube, the external flow restrictor configured to provide or remove an external pressure to the first tube that respectively close or open a fluid passageway of the first tube.

Clause 16. The infusion pump of any of the proceeding Clauses, further comprising a controller chip configured to operate a valve to control the first flow rate of the fluid.

Clause 17. The infusion pump of any of the proceeding Clauses, wherein the second flow rate such that it is no greater than 5 mL/hr.

Clause 18. The infusion pump of any of the proceeding Clauses, wherein the one or more components configured to connect with the outlet of the second tube include a skin patch, a needle, and a catheter.

Clause 19. The infusion pump of any of the proceeding Clauses, wherein: the elastic component is formed of a single layer membrane; and the housing includes an inlet for receiving the fluid, the fluid received via the inlet expanding the elastic component and generating the potential energy stored by the elastic component.

Clause 20. The infusion pump of Clause 19, wherein the single layer membrane is an elastomeric membrane.

Clause 21. The infusion pump of any of the proceeding Clauses, wherein the elastic component is configured to expand to hold a volume of at least 50 mL of the fluid.

Clause 22. The infusion pump of any of the proceeding Clauses, wherein: the housing includes: a first portion that includes a first and second surface, wherein: the first surface includes the outlet of the housing for distributing the fluid, and the second surface, opposite the first surface, includes the elastic component coupled between a first ring and a second ring affixed the second surface; a second portion that is configured to house the second surface of the first portion, wherein the first portion and the second portion are coupled.

Clause 23. A method of infusing fluid to a patient, the method comprising: at an infusion pump comprising: a housing including an elastic component; a first tube fluidically coupled to the housing via an outlet of the housing, an air filter fluidically coupled to a distal end of the first tube via an air filter inlet, a second tube fluidically coupled to the air filter via an air filter outlet, and an outlet of the second tube fluidically coupled to one or more components; expanding the elastic component with the fluid to store potential energy generated by the fluid within the infusion pump; conducting, from the first tube, fluid from the housing at a first flow rate based, in part, on the potential energy stored by the elastic component; expelling air from the fluid via the one or more air vents of the air filter, wherein the air is expelled substantially upstream such that the fluid exiting the air filter is primed without air; adjusting the first flow rate of the fluid conducted from the housing, via the first tube, to a second flow rate, the second flow rate based, at least in part, on an inner diameter of the second tube; and distributing the fluid to a user via the one or more components.

Further Consideration:

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other implementations.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and implementations of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An infusion pump comprising:
    a housing including an elastic component configured to expand and store potential energy generated by a fluid within the infusion pump, and
    a first tube fluidically coupled to an outlet of the housing, the first tube configured to conduct the fluid from the housing at a first flow rate;
    a flow restrictor component within the first tube, the flow restrictor having a diameter less than an inner diameter of the first tube and comprising a pin configured to change the shape of the fluid from a cylindrical shape to a torus shape, wherein the first flow rate is based on the potential energy stored by the elastic component and on a radius or a length of the pin;
    an air filter fluidically coupled to a distal end of the first tube via an air filter inlet, the air filter configured to expel air from the fluid via one or more air vents, wherein the air is expelled substantially upstream such that the fluid exiting the air filter is primed without air;
    a second tube fluidically coupled to the air filter via an air filter outlet, wherein:
        the second tube configured to adjust the first flow rate of the fluid conducted from the housing, via the first tube, to a second flow rate, the second flow rate based, at least in part, on an inner diameter of the second tube, and
        an outlet of the second tube is configured to fluidically couple to one or more components for distributing the fluid to a user.

2. The infusion pump of claim 1, wherein the inner diameter of the second tube is no greater than 0.0075 inches.

3. The infusion pump of claim 2, the second tube is a predetermined length, and the second flow rate is further based on the predetermined length.

4. The infusion pump of claim 3, wherein an inner diameter of the first tube and the inner diameter of the second tube are the same.

5. The infusion pump of claim 3, wherein an inner diameter of the first tube and the inner diameter of the second tube are distinct.

6. The infusion pump of claim 1, wherein the pin has a predetermined radius, and the first flow rate is further based, in part, on the predetermined radius of the pin.

7. The infusion pump of any of claim 1, wherein the pin has a predetermined length, and the first flow rate is further based, in part, on the predetermined length of the pin.

8. The infusion pump of claim 1, wherein the flow restrictor component is unfixed within the first tube and configured to move a length of the first tube.

9. The infusion pump of claim 1, wherein the air filter includes a membrane filter that is configured to remove one or more contaminants and particulates from the fluid.

10. The infusion pump of claim 1, further comprising a controller chip configured to operate a valve to control the first flow rate of the fluid.

11. The infusion pump of claim 1, wherein the second flow rate such that it is no greater than 5 mL/hr.

12. The infusion pump of claim 1, wherein the one or more components configured to connect with the outlet of the second tube include a skin patch, a needle, and a catheter.

13. The infusion pump of claim 1, wherein:
    the elastic component is formed of a single layer membrane; and
    the housing includes an inlet for receiving the fluid, the fluid received via the inlet expanding the elastic component and generating the potential energy stored by the elastic component.

14. The infusion pump of claim 13, wherein the single layer membrane is an elastomeric membrane.

15. The infusion pump of claim 13, wherein the elastic component is configured to expand to hold a volume of at least 50 mL of the fluid.

16. The infusion pump of claim 1, wherein:
the housing includes:
- a first portion that includes a first and second surface, wherein:
  - the first surface includes the outlet of the housing for distributing the fluid, and
  - the second surface, opposite the first surface, includes the elastic component coupled between a first ring and a second ring affixed the second surface;
- a second portion that is configured to house the second surface of the first portion, wherein the first portion and the second portion are coupled.

17. A method of infusing fluid to a patient, the method comprising:
at an infusion pump comprising:
- a housing including an elastic component;
- a first tube fluidically coupled to the housing via an outlet of the housing,
- a flow restrictor component within the first tube, the flow restrictor having a diameter less than an inner diameter of the first tube and comprising a pin configured to change the shape of a fluid flowing within the first tube from a cylindrical shape to a torus shape,
- an air filter fluidically coupled to a distal end of the first tube via an air filter inlet,
- a second tube fluidically coupled to the air filter via an air filter outlet, and
- an outlet of the second tube fluidically coupled to one or more components;

expanding the elastic component with the fluid to store potential energy generated by the fluid within the infusion pump;

conducting, from the first tube, the fluid from the housing at a first flow rate based, in part, on the potential energy stored by the elastic component and on a radius or a length of the pin;

expelling air from the fluid via one or more air vents of the air filter, wherein the air is expelled substantially upstream such that the fluid exiting the air filter is primed without air;

adjusting the first flow rate of the fluid conducted from the housing, via the first tube, to a second flow rate, the second flow rate based, at least in part, on an inner diameter of the second tube; and distributing the fluid to a user via the one or more components.

* * * * *